United States Patent [19]

Kasai

[11] 4,077,720
[45] Mar. 7, 1978

[54] SPECTROSCOPIC AUTO ELLIPSOMETER
[75] Inventor: Toshiyuki Kasai, Matsudo, Japan
[73] Assignee: Nippon Kogaku K.K., Tokyo, Japan
[21] Appl. No.: 722,107
[22] Filed: Sep. 10, 1976
[30] Foreign Application Priority Data Sep. 26, 1975 Japan .................................. 50-115644

[51] Int. Cl.² .......................................... G01N 21/40
[52] U.S. Cl. ................................................. 356/118
[58] Field of Search ............................... 356/114–118; 250/225

[56] References Cited

U.S. PATENT DOCUMENTS

| 3,741,661 | 6/1973 | Yamamoto et al. | 356/117 |
| 3,992,104 | 11/1976 | Watanabe | 356/117 |

OTHER PUBLICATIONS

Jungk, G. "Determination of Optical Constants: A Null-Method", Phys. Stat. Sol. (a) vol. 3, 1970, pp. 965–970.

Primary Examiner—John K. Corbin
Assistant Examiner—Wm. H. Punter
Attorney, Agent, or Firm—Fitzpatrick, Cella, Harper & Scinto

[57] ABSTRACT

A spectroscopic auto ellipsometer for measuring two variables of polarized light (principal angle of incidence and amplitude-reflection ratio angle) by using the principal angle of incidence method comprises an illumination optical system, a polarizer set to a predetermined azimuth and rotatable with respect to the optical axis of the illumination optical system, a table supporting thereon a sample and rotatable for varying the angle of incidence at which linearly polarized light passed through the polarizer impinges on the sample, an analyzer rotatable at a predetermined velocity on the reflection optical axis from the sample, photoelectric converter means for converting the intensity of light emergent from the analyzer into electrical signal, holder means holding the analyzer and the photoelectric converter means integrally with each other and operatively associated with the sample supporting table so as to be rotated through an angle of $\pm 2\theta$ for rotation of the sample supporting table through an angle of $\pm \theta$, reference signal generating means for generating, during rotation of the analyzer, reference signal at at least one of $\pm 90°$ azimuths on the Poincare's sphere with respect to the predetermined azimuth of the polarizer, first control means for comparing the output of the photoelectric converter means with the reference signal from the reference signal generating means and for rotating the sample supporting table until the maximum or the minimum value of the output from the photoelectric converter means is coincident with the reference signal, and second control means operable after completion of the control by the first control means to rotate the polarizer from its predetermined azimuth until the output of the photoelectric converter means assumes a predetermined constant value.

6 Claims, 14 Drawing Figures

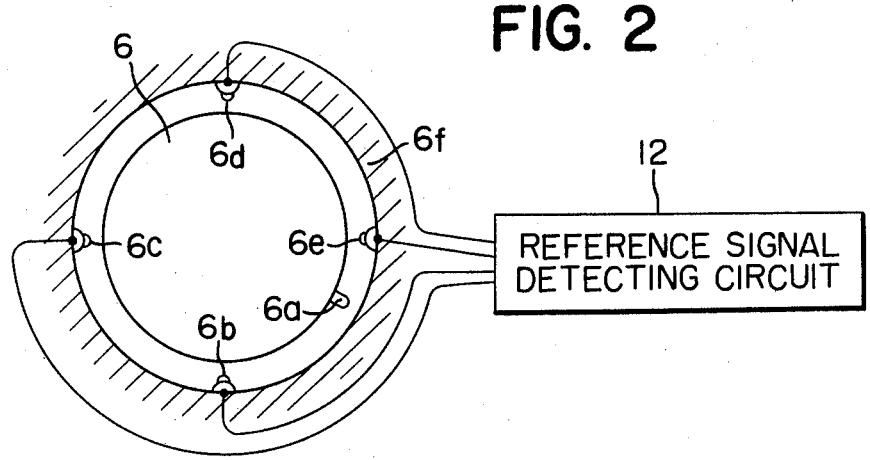
FIG. 2
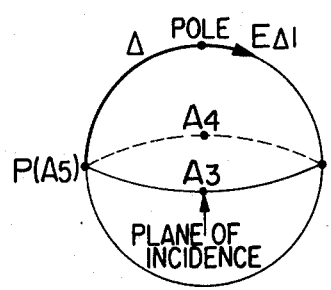
FIG. 3-a
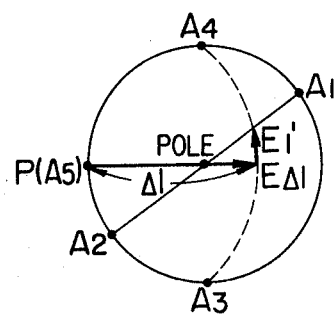
FIG. 3-b
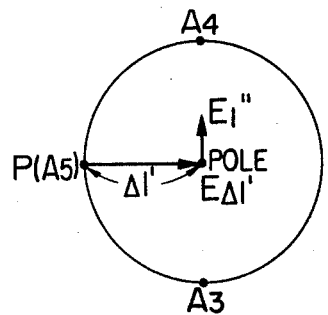
FIG. 3-c
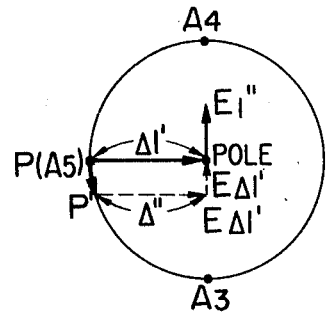
FIG. 3-d

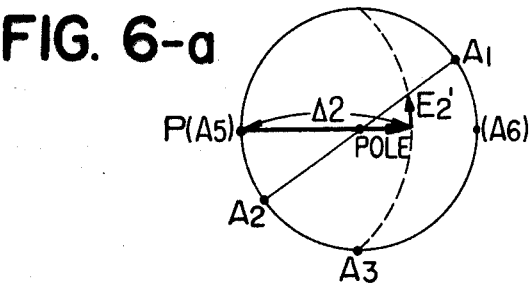
FIG. 6-a
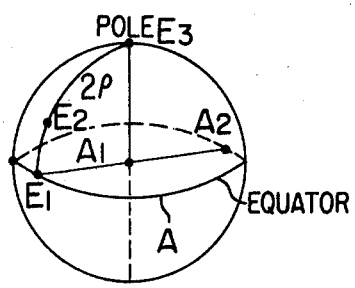
FIG. 4
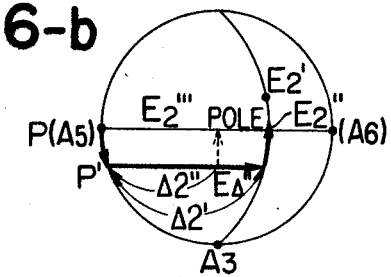
FIG. 6-b
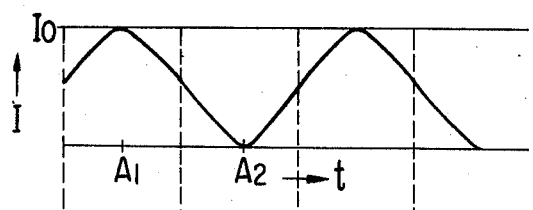
FIG. 5-a
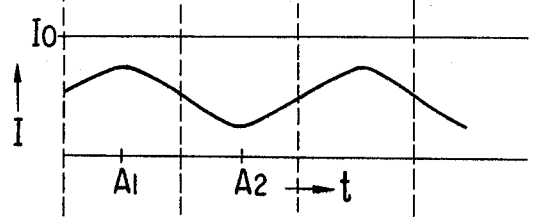
FIG. 5-b
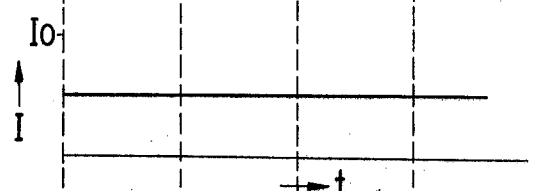
FIG. 5-c
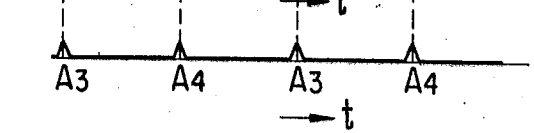
FIG. 5-d

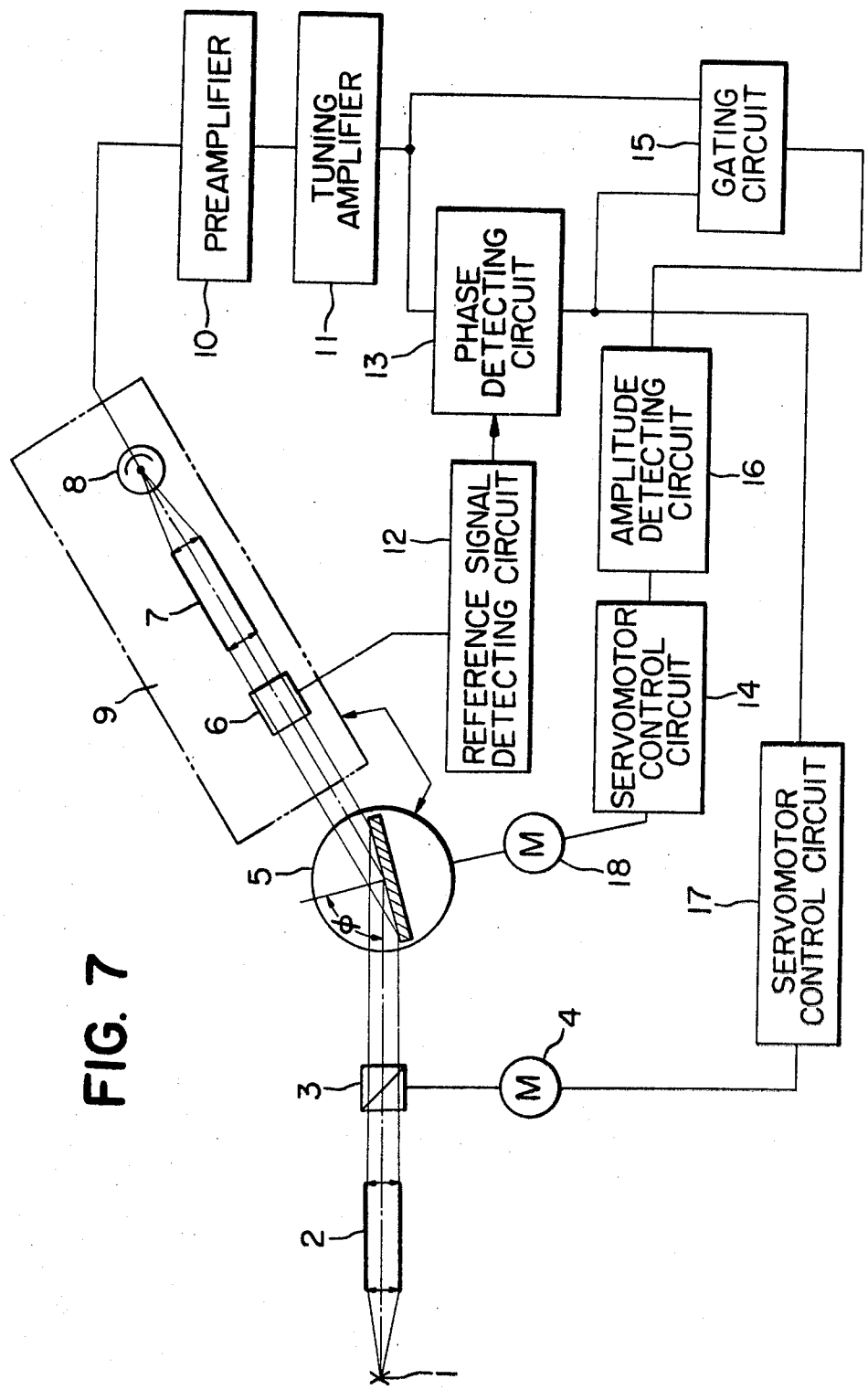

SPECTROSCOPIC AUTO ELLIPSOMETER

BACKGROUND OF THE INVENTION

1. Field of the Invention

This invention relates to a polarimeter for effecting the analysis of polarized light, and more particularly to a polarimeter which enables the analysis of polarized light in any wavelength to be achieved by utilization of the principal angle of incidence method known as a method of analysing polarized light in any wavelength.

2. Description of the Prior Art

In the analysis of polarized light, the known technique of measuring the variations in polarization resulting from reflection has resorted to the use of means such as a polarizer, a quarter wavelength plate, an analyser, etc., rotating the polarizer and the analyser, obtaining then the angles of rotation of the polarizer and analyser from the condition under which the reflected light from a sample is extinguished by the analyser, and calculating two variables of polarized light (phase difference $\Delta$ and amplitude-reflection ratio angle $\Psi$). However, such means have been disadvantageous in that the use of a polarizing element like the quarter wavelength plate, which depends on wavelength, has limited the wavelength used and the analysis of polarized light by any other wavelength has been impossible.

SUMMARY OF THE INVENTION

The present invention has, for its object, to eliminate the above-noted disadvantages existing in the analysis of polarized light and to provide an ellipsometer which enables two variables of polarized light (principal angle of incidence $\Phi$ and amplitude-reflection ratio angle $\Psi$) to be obtained by using the principal angle of incidence method which does not use any polarizing element that depends on wavelength.

According to the present invention, the ellipsometer comprises an illumination optical system, a polarizer set to a predetermined azimuth and mounted for rotation with respect to the optical axis of the illumination optical system, a table supporting thereon a sample and rotatably mounted for varying the angle of incidence at which linearly polarized light passed through the polarizer impinges on the sample, an analyser rotatable at a predetermined angular velocity on the reflection optical axis from the sample, photoelectric converter means for converting the intensity of light emergent from the analyser into electrical signal, holder means holding the analyser and the photoelectric converter means integrally with each other and operatively associated with the sample supporting table so as to be rotated through an angle of $\pm 2\theta$ for rotation of the sample supporting table through an angle of $\pm \theta$, reference signal generating means for generating, during rotation of the analyser, a reference signal at at least one of $\pm 90°$ azimuths on the Poincare's sphere with respect to the predetermined azimuth of the polarizer, first control means for comparing the output of the photoelectric converter means with the reference signal from the reference signal generating means and for rotating the sample supporting table until the maximum or the minimum value of the output from the photoelectric converter means is coincident with the reference signal, and second control means operable after completion of the control by the first control means to rotate the polarizer from its predetermined azimuth until the output of the photoelectric converter means assumes a predetermined constant value.

The invention will become more fully apparent from the following detailed description of some embodiments thereof taken in conjunction with the accompanying drawings.

BRIEF DESCRIPTION OF THE DRAWINGS

FIG. 2 illustrates the reference signal detecting circuit in FIG. 1;

FIGS. 3-a, 3-b, 3-c, 3-d, FIG. 4, FIGS. 5-a, 5-b, 5-c, 5-d and FIG. 6-a, 6-b illustrate the measurement principle in FIG. 1;

FIG. 7 schematically shows a second embodiment of the present invention in which the measurement principle of the invention is applied to an actual apparatus.

DESCRIPTION OF THE PREFERRED EMBODIMENTS

Figure 1:
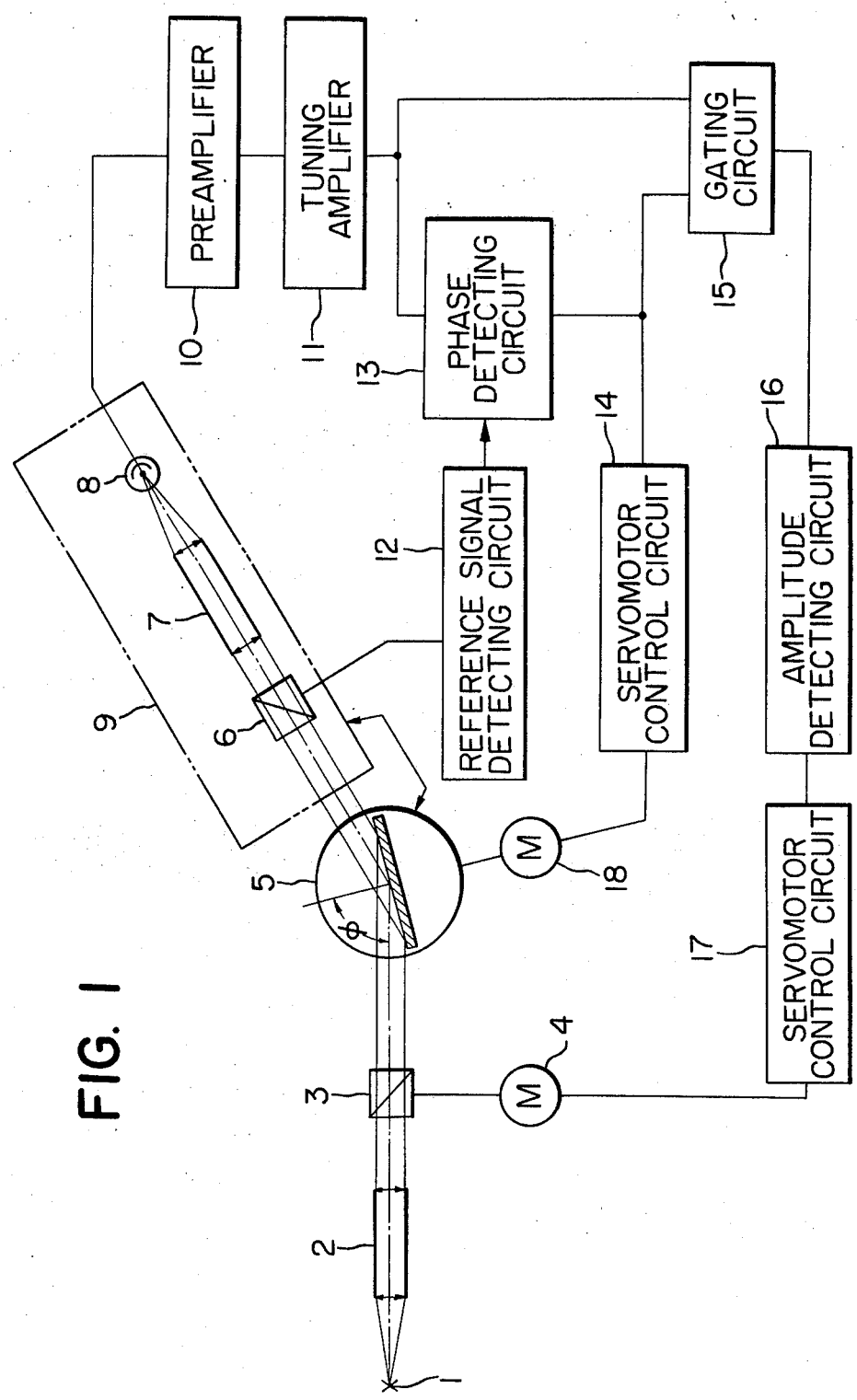
FIG. 1 schematically shows a first embodiment of the present invention.

Referring to FIG. 1, there is shown a first embodiment of the present invention. Light emergent from a spectroscope (not shown) set to any desired wavelength is directed through the emergence slit 1 of the spectroscope to an illumination optical system 2 and further transmitted through a polarizer 3 set to, for example, $-45°$ with respect to the plane of incidence, where the light is made into linearly polarized light and reflected by a sample on a sample supporting table 5, whereupon the polarization of the light is changed. The polarizer 3 is always set to $-45°$ with respect to the plane of incidence during initiation of measurement by providing a position sensor (not shown), but is also rotatable about the optical axis by a servomotor 4 provided as a separate mechanism. The light reflected and changed in polarization by the sample is directed to a light receiving system 9 which comprises an analyser 6, an observation optical system 7 and a photoelectric conversion element 8.

Since the light receiving system 9 is operatively associated with the sample supporting table 5 and is rotatable through an angle of $\pm 2\theta$ in response to rotation of the sample supporting table 5 through an angle of $\pm \theta$, the reflected light from the sample is assuredly directed to the light receiving system 9. This reflected light is transmitted through the analyser 6 adapted to continue to rotate about the optical axis at an arbitrarily predetermined angular velocity $\omega$ during the measurement, and passed through the observation optical system 7 to the photoelectric conversion element 8, by which the light is converted into an electrical signal proportional to its intensity. The electrical signal is amplified by a preamplifier 10, and then further amplified by a tuning amplifier 11 having a tuning frequency double the rotation frequency $\omega/2\pi$ of the analyser 6. On the other hand, a reference signal detecting circuit 12 generates a reference signal when a projection 6a (FIG. 2) formed on an outer peripheral portion of the analyser 6 makes contact with a switch 6b held by a casing 6f. The positional relationship between the projection 6a and the switch 6b is such that they contact each other when the azimuth of the analyser 6 is coincident with the plane of incidence. Further, the projection 6a makes contact with switches 6c, 6d and 6e in succession upon each quarter of one complete rotation of the analyser 6 and accordingly, the reference signal detecting circuit 12 generates reference signals in succession.

The output of the tuning amplifier 11 is passed to a phase detecting circuit 13, by which said output is compared with the reference signals generated by the reference signal detecting circuit 12. The phase detecting circuit 13 continues to send a signal to a servomotor control circuit 14 to thereby operate the servomotor to rotate the sample supporting table 5 until the maximum value of the output of the tuning amplifier 11 is coincident with a certain one of the reference signals and the minimum value of said output is coincident with a reference signal adjacent to said certain one of the reference signals. In some particular cases, the effort to make the maximum and the minimum value of the output of the tuning amplifier 11 coincident with the aforementioned reference signals may result in zero output of the tuning amplifier 11, but this may be taken as meaning that the maximum and the minimum value have coincident with the reference signals by said output becoming zero. When the above-described conditions are satisfied, the phase detecting circuit 13 sends a stop signal to the servomotor control circuit 14 to stop the sample supporting table 5. When the sample supporting table 5 has been stopped, the reflected light from the sample is in such a polarized condition that the phase difference Δ is 90°, and the angle of incidence Φ at that time is the principal angle of incidence.

The output of the tuning amplifier 11 and the output of the phase detecting circuit 13 provide inputs to a single gating circuit 15, which is operable to transmit the output of the tuning amplifier 11 to an amplitude detecting circuit 16 upon reception of the stop signal generated by the phase detecting circuit 13. When the output of the tuning amplifier 11 is a periodically varying signal, the amplitude detecting circuit 16 sends a signal to the servomotor control circuit 17 to operate the same, but when the output of the tuning amplifier 11 has come to assume a predetermined constant value as shown in FIG. 5-c, the amplitude detecting circuit 16 sends no signal to the servomotor control circuit 17 to thereby stop the servomotor. The polarizer 3 is rotated about the optical axis as long as the servomotor is in operation, and, becomes stationary as soon as the servomotor 4 is stopped. Here, by obtaining P which is the azimuth of the polarizer 3 with respect to the plane of incidence when it has become stationary after rotation, the amplitude-reflection ratio Ψ may be calculated from:

$$\Psi = \tan^{-1} 1/\tan (P)$$

In the foregoing, the azimuth of the polarizer 3 during initiation of the measurement has been described to be set to −45° with respect to the plane of incidence, whereas the azimuth of the polarizer 3 is not restricted thereto but may be any azimuth if it is clear during the initiation of the measurement. Also, the above-described embodiment is arranged such that reference signals are generated at any of ±90° azimuths on the Poincare's sphere with respect to the azimuth of the polarizer 3, that is, switches 6b, 6c, 6d and 6e are provided.

With such an arrangement, any irregularity in the rotation of the analyser 6 may be compensated for. However, it is sufficient if reference signals are generated at the azimuths of ±90° on the Poincare's sphere with respect to the predetermined azimuth of the polarizer 3. In other words, it is sufficient if the switches 6b and 6d or 6c and 6e are provided. In such an arrangement, comparison will be made between the reference signal and the maximum or the minimum phase of the output signal from the tuning amplifier.

The principle of measurement in the above-described first embodiment will hereinafter be explained by reference to FIGS. 3 to 5.

It is known that the intensity I of the emergent light from the analyser is expressed as $I = \cos^2 \rho$ if $2\rho$ is the distance on the surface of the Poincare's sphere between the point representing the azimuth on the sphere of the polarized incident light impinging on the analyser and the point representing the azimuth of the analyser on the equator. Thus, it will be seen in FIG. 4 that if the polarization of the incident light impinging on the analyser is the linearly polarized light as indicated at $E_1$ on the equator and when the analyser revolving on the equator at an angular velocity $\omega$ reaches a point $A_1$ which is identical with $E_1$, then the intensity I of the emergent light from the analyser assumes its maximum value, and that when the analyser comes to a point $A_2$ which is diametrically opposite to the point $A_1$ with respect to the pole, the intensity I of the emergent light assumes its minimum value. That is, the intensity I is periodically varied as shown in FIG. 5-a.

If the incident light impinging on the analyser is elliptically polarized light, such light may assume the other points than the pole on the Poincare's sphere and points on the equator, and these points may typically be represented by a point $E_2$ in FIG. 4. As in the case of the above-described linearly polarized light, the intensity I of the emergent light from the analyser assumes its maximum value when the analyser has come to the point $A_1$ and assumes its minimum value when the analyser has come to the point $A_2$. There is thus obtained the graph of FIG. 5-b wherein the intensity I is periodically varied. If the incident light impinging on the analyser is circularly polarized light, such light is represented by the pole $E_3$ on the Poincare's sphere in FIG. 4. In this case, even if the analyser revolves on the equator, the intensity I of the emergent light from the analyser assumes a predetermined value irrespective of the position of the revolving analyser because the distance between the pole and the equator is invariable (see FIG. 5-c). In the present invention, the polarization of the incident light impinging on the analyser 6 is observed in terms of variations in intensity of the emergent light, from the relation between the graphs of FIGS. 5-a, 5-b, 5-c obtained in the foregoing description and the graph of FIG. 5-d showing the reference signals.

In FIG. 3-a which shows the Poincare's sphere, the light leaving the illuminating optical system 2 is transmitted through the polarizer 3 with its azimuth inclined by −45° with respect to the plane of incidence, whereby such light becomes the linearly polarized light as represented by a point $A_5$. The linearly polarized light represented by the point $A_5$ is reflected by the sample to create a phase difference Δ and displaced to a position as indicated at $E\Delta_1$ while, at the same time, the light is varied in amplitude-reflection ratio angle Ψ and displaced to a point $E_1'$ in FIG. 3-b which is a view as seen from the pole in FIG. 3-a. The elliptically polarized light represented by the point $E_1'$ is incident on the analyser 6. When the analyser 6a revolving on the equator, has brought its azimuth to a point $A_1$, the intensity I of the emergent light therefrom exhibits its maximum value and when the azimuth of the analyser has come to a point $A_2$, the intensity I of the emergent light therefrom exhibits its maximum value. Thus, the intensity I is periodically varied as shown in FIG. 5-b. Now, when the signal from the phase detecting circuit 13 enters the servomotor control circuit 14, the servomotor 18 is operated to rotate the sample supporting table 5, thus varying the angle of incidence Φ of the light impinging on the sample. The phase difference Δ is varied accordingly. When the phase difference $\Delta_1$ is varied to $\Delta_1'$ as shown in FIG. 3-c wherein Δ=90°, the intensity I of the emergent light from the analyser 6 exhibits its minimum value when the azimuth of the analyser 6 has become coincident with a point $A_3$ representing the plane of incidence, and the intensity I exhibits its maximum value when the azimuth of the analyser 6 has come to a point $A_4$ diametrically opposite to the point $A_3$ with respect to the pole. That is, the phase detecting circuit 13 generates the aforementioned stop signal when there is coincidence between the reference signals generated at the points $A_3$ and $A_4$ and the maximum and the minimum of the intensity of the emergent light and thus, the sample supporting table 5 is stopped from rotating when the polarized incident light $E_1'$ of FIG. 3-b impinging on the analyser 6 is displaced to a point $E_1''$ as indicated in FIG. 3-c.

By the stop signal, the gating circuit 15 is opened to permit the signal from the amplitude detecting circuit 16 to enter the servomotor control circuit 17, whereupon the servomotor 4 is operated to rotate the polarizer 3. The amplitude detecting circuit 16 is designed such that when the input thereto has become zero, it sends a signal to the servomotor control circuit 17 to stop the servomotor 4. The incident light impinging on the analyser 6 when the servomotor 4 is stopped is circularly polarized light. Thus, the azimuth of the polarizer 3 has been displaced from P to P' on the equator as shown in FIG. 3-d, and correspondingly $E\Delta_1'$ and $E_1''$ have been displaced to $E\Delta_1''$ and $E\Delta_1'$, respectively.

In the foregoing description, the sample supporting table was first rotated by the phase detecting circuit 13 until the maximum and the minimum value of the output of the tuning amplifier 11 became coincident with the reference signals, whereby the principal angle of incidence Φ was obtained and thereafter, the amplitude detecting circuit 16 sent a signal to the servomotor control circuit 17 to operate the servomotor 4 and thereby rotate the polarizer 3, and when the output of the tuning amplifier 11 became zero, the polarizer 3 was stopped from rotating and the amplitude-reflection ratio angle Ψ was obtained from the then angle of rotation of the polarizer 3. A similar construction may be applied even when the polarizer 3 is first rotated to obtain the amplitude-reflection ratio angle Ψ, whereafter the principal angle of incidence Φ is obtained. That is, in FIG. 6-a which is a view of the Poincare's sphere as seen from its pole, the light transmitted through the polarizer P with its azimuth disposed at −45° with respect to a point $A_3$ representing the plane of incidence becomes linearly polarized light represented by a point $A_5$, and then reflected by the sample to become elliptically polarized light represented by $E_2'$. The reference signal detecting circuit is prearranged such that when the analyser has assumed on azimuth of −45° with respect to the plane of incidence, a reference signal is generated and thereafter, a reference signal is generated upon each quarter of one complete rotation of the analyser. Thus the reference signal generating means generates during rotation of the analyser, a reference signal at at least one of the same azimuths as the predetermined azimuth of the polarizer and an azimuth of 180° with respect thereto on the Poincare's sphere. In FIG. 6-b, as the polarizer revolving on the equator is displaced from P to P', $E_2'$ is displaced to $E_2''$. Thus, when the analyser revolving on the equator has come to an azimuth represented by a point $A_6$, the phase detecting circuit makes the maximum output from the tuning amplifier correspond to a reference signal and when the analyser has come to an azimuth represented by a point $A_5$, the phase detecting circuit makes the minimum output from the timing amplifier correspond to a reference signal adjacent to the aforementioned reference signal, whereby the position of $E_2''$ may be confirmed to thereby enable the amplitude-reflection ratio angle Ψ to be obtained. Further, if the angle of incidence of the light impinging on the sample is varied with the polarizer remaining fixed at said azimuth P', $E_2''$ is displaced to $E_2'''$ which is the pole on the Poincare's sphere, and this is confirmed by the amplitude detecting circuit.

FIG. 7 shows a second embodiment of the present invention which is an application of the above-described measurement principle to an actual apparatus. In FIG. 2 which shows the construction of the reference signal detecting circuit 12, the positional relation of the projection 6a with the switches 6b, 6c, 6d, 6e is such that when the azimuth of the analyser 6 has become −45° with respect to the plane of incidence, a reference signal is generated and thereafter, a reference signal is generated upon each quarter of one complete rotation of the analyser. The output of the tuning amplifier 11 is compared with the reference signals by the phase detecting circuit 13. The phase detecting circuit 13 continues to send an operating signal to the servomotor control circuit 17 to thereby operate the servomotor 4 to rotate the polarizer 3 until the maximum value of the output of the tuning amplifier 11 coincides with a certain one of said reference signals and the minimum value of said output coincides with a reference signal adjacent to said certain one of the reference signals. When the above-described conditions are satisfied, the phase detecting circuit 13 generates a stop signal for stopping the servomotor 4 to thereby stop the polarizer 3 from rotating. The output of the tuning amplifier 11 and the output of the phase detecting circuit 13 are applied as input to the gating circuit 15, which transmits the output of the tuning amplifier 11 to the amplitude detecting circuit 16 upon reception of the stop signal generated by the phase detecting circuit 13. The amplitude detecting circuit 16 continues to send an operating signal to the servomotor control circuit 14 until the output of the tuning amplifier 11 assumes a predetermined constant value, whereupon the amplitude detecting circuit generates a stop signal. Upon reception of the afore-mentioned operating signal, the servomotor control circuit 14 operates the servomotor to rotate the sample supporting table 5. Upon reception of the stop signal generated by the amplitude detecting circuit 16, the servomotor control circuit 14 stops the servomotor from rotating, thereby rendering the sample supporting table 5 stationary.

By the above-described operation, the amplitude-reflection ratio angle Ψ may be obtained from the azimuth of the polarizer 3, after rotation, with respect to the plane of incidence and the principal angle of incidence Φ may be obtained from the angle of incidence of the sample supporting table 5 after it is stopped.

Thus, the present invention enables the analysis of polarized light in any wavelength because it does not employ in its optical system any optical element such as quarter wavelength plate which depends on wavelength.

Moreover, the present invention enables the two variables of polarized light (principal angle of incidence Φ and amplitude-reflection ratio angle Ψ) to be obtained through such a simple operation that the periodical variation in intensity of the output light from the analyser is compared with reference signals to thereby rotate the sample supporting table or the polarizer and then, either the sample supporting table or the polarizer which has not been rotated is rotated so that the intensity of said output light assumes a predetermined constant value.

I claim:

1. A spectroscopic auto ellipsometer for measuring two variables of polarized light (principal angle of incidence Φ and amplitude-reflection ratio angle Ψ) by using the principal angle of incidence method, comprising:

an illumination optical system;

a polarizer set to a predetermined azimuth and mounted for rotation with respect to the optical axis of said illumination optical system;

a table supporting thereon a sample and rotatably mounted for varying the angle of incidence at which linearly polarized light passed through said polarizer impinges on said sample;

an analyser rotatable at a predetermined angular velocity on the reflection optical axis from said sample;

photoelectric converter means for converting the intensity of light emergent from said analyser into electrical signal;

holder means holding said analyser and said photoelectric converter means integrally with each other and operatively associated with said sample supporting table so as to be rotated about the center of rotation of said sample supporting table through an angle of ±2θ for rotation of said sample supporting table through an angle of ± θ;

reference signal generating means for generating, during rotation of said analyser, a reference signal at at least one of ±90° azimuths on the Poincare's sphere with respect to the predetermined azimuth of said polarizer;

first control means for comparing the output of said photoelectric converter means with the reference signal from said reference signal generating means and for rotating said sample supporting table until the maximum or the minimum value of said output from said photoelectric converter means is coincident with said reference signal; and second control means operable after completion of the control by said first control means to rotate said polarizer from its predetermined azimuth until the output of said photoelectric converter means assumes a predetermined constant value.

2. An ellipsometer according to claim 1, wherein said first control means comprises:

a phase detecting circuit for comparing the phase of the output signal of said photoelectric converter means with the phase of said reference signal and for generating an operating signal when said maximum or said minimum value is out of phase with said reference signal and generating a stop signal when said maximum or said minimum value is in phase with said reference signal; and first servo control means for rotating said sample supporting table as long as it receives the operating signal from said phase detecting circuit and for stopping said sample supporting table upon reception of said stop signal.

3. An ellipsometer according to claim 2, wherein said second control means comprises:

a gating circuit connected to said phase detecting circuit and said photoelectric converter means to pass therethrough the signal from said photoelectric converter means upon reception of the stop signal from said phase detecting circuit;

an amplitude detecting circuit connected to said gating circuit to generate an operating signal as long as the output signal from said photoelectric converter means is a periodically varying signal and to stop generating said operating signal when said output signal assumes a predetermined constant value; and a second servo control circuit for rotating said polarizer as long as it receives the operating signal from said amplitude detecting circuit.

4. A spectroscopic auto ellipsometer for measuring two variables of polarized light (principal angle of incidence Φ and amplitude-reflection ratio angle Ψ) by using the principal angle of incidence method, comprising:

an illumination optical system;

a polarizer set to a predetermined azimuth and mounted for rotation with respect to the optical axis of said illumination optical system;

a table supporting thereon a sample and rotatably mounted for varying the angle of incidence at which linearly polarized light passed through said polarizer impinges on said sample;

an analyser rotatable at a predetermined angular velocity on the reflection optical axis from said sample;

photoelectric converter means for converting the intensity of light emergent from said analyser into electrical signal;

holder means holding said analyser and said photoelectric converter means integrally with each other and operatively associated with said sample supporting table so as to be rotated about the center of rotation of said sample supporting table through an angle of ±2θ for rotation of said sample supporting table through an angle of ±θ;

reference signal generating means for generating, during rotation of said analyser, a reference signal at at least one of the same azimuths as the predetermined azimuth of said polarizer and an azimuth of 180° with respect thereto on the Poincare's sphere;

first control means for comparing the output of said photoelectric converter means with the reference signal from said reference signal generating means and for rotating said polarizer from said predetermined azimuth thereof until the maximum or the minimum value of said output from said photoelectric converter means is coincident with said reference signal; and second control means operable after completion of the control by said first control means to rotate said sample supporting table until the output of said photoelectric converter means assumes a predetermined constant value.

5. An ellipsometer according to claim 4, wherein said first control means comprises:

a phase detecting circuit for comparing the phase of the output signal of said photoelectric converter means with the phase of said reference signal and for generating an operating signal when said maximum or said minimum value is out of phase with said reference signal and generating a stop signal when said maximum or said minimum value is in phase with said reference signal; and first servo control means for rotating said polarizer table as long as it receives the operating signal from said phase detecting circuit and for stopping said sample supporting table upon reception of said stop signal.

6. An ellipsometer according to claim 5, wherein said second control means comprises:

a gating circuit connected to said phase detecting circuit and said photoelectric converter means to pass therethrough the signal from said photoelectric converter means upon reception of the stop signal from said phase detecting circuit;

an amplitude detecting circuit connected to said gating circuit to generate an operating signal as long as the output signal from said photoelectric converter means is a periodically varying signal and to stop generating said operating signal when said output signal assumes a predetermined constant value; and a second servo control circuit for rotating said sample supporting table as long as it receives the operating signal from said amplitude detecting circuit.

* * * * *